United States Patent [19]

Nottingham

[11] Patent Number: 5,142,230

[45] Date of Patent: Aug. 25, 1992

[54] SCANNING DEVICE AND METHOD FOR AUTOMATED EDDY CURRENT INSPECTION OF ELECTRICAL GENERATOR RETAINING RINGS

[75] Inventor: Lawrence D. Nottingham, Charlotte, N.C.

[73] Assignee: Electric Power Research Institute, Inc., Palo Alto, Calif.

[21] Appl. No.: 788,330

[22] Filed: Nov. 5, 1991

[51] Int. Cl.$^5$ .............................................. G01N 27/90
[52] U.S. Cl. ................................................... 324/262
[58] Field of Search ............................... 324/234–242, 324/260–262, 219–221

[56] References Cited

U.S. PATENT DOCUMENTS

| | | | |
|---|---|---|---|
| 3,921,065 | 11/1975 | Rawlins et al. | 324/238 |
| 4,142,154 | 2/1979 | Couchman | 324/238 X |
| 4,454,473 | 6/1984 | Rosauer | 324/262 |
| 4,468,620 | 8/1984 | Vaerman | 324/262 X |
| 4,739,273 | 4/1988 | Petersen et al. | 324/262 X |
| 4,785,243 | 11/1988 | Abramczyk | 324/232 |
| 4,803,563 | 2/1989 | Dailey et al. | 324/262 X |
| 4,806,863 | 2/1989 | White | 324/238 |
| 4,855,677 | 8/1989 | Clark, Jr. et al. | 324/238 |
| 5,059,904 | 10/1991 | Mazzone et al. | 324/262 X |
| 4,808,927 | 2/1989 | Cecco et al. | 324/220 |

OTHER PUBLICATIONS

J. A. Jones Applied Research Company, "The Eddy-Current Technique for Nondestructive Evaluation of Generator Retaining Rings"; May 1988, pp. i-10/1.
J. A. Jones Applied Research Company, "A Feature-Based Eddy-Current Imaging System for Personal Computers"; EPRI NP-6167; Mar. 1989, pp. i-7/1.
Reinhart, Eugene R. et al.; "Mechanized Automated Ultrasonic and Eddy Current Inspection of Retainer Rings", No Date, pp. 1-13.
Viertl, J. R. M. et al; "General Electric Retaining Ring Inspection, Evaluation, and Disposition Service", No Date, pp. 1-16.

Primary Examiner—Kenneth A. Wieder
Assistant Examiner—W. S. Edmonds
Attorney, Agent, or Firm—Flehr, Hohbach, Test, Albritton & Herbert

[57] ABSTRACT

A scanning device for automated eddy current inspection of retaining rings is disclosed. The scanning device supports an eddy current probe inside the retaining rings and moves the probe automatically in an axial and rotational path within the rings to scan the entire surface of the rings.

15 Claims, 3 Drawing Sheets

SCANNING DEVICE AND METHOD FOR AUTOMATED EDDY CURRENT INSPECTION OF ELECTRICAL GENERATOR RETAINING RINGS

FIELD OF THE INVENTION

This invention relates generally to a scanning device and method for automated eddy current inspection of electrical generator retaining rings.

BACKGROUND OF THE INVENTION

Retaining rings are cylindrical steel components mounted to either end of an electrical generator rotor. At the rotor ends, copper windings exit slotted portions on the rotor body and form unsupported arcs to the opposite side of the rotor's magnetic poles before they re-enter other slotted portions These arcs are known as the endturns of the windings. The retaining rings contain and support these end-turns against rotational forces.

Other components made of similar materials and used in similar rotating applications include zone cooling baffles and retaining rings on exciters. Because of their similarity in function, failure mechanisms, and necessary care, all such components are included in the general description of a retaining ring.

Retaining rings typically suffer from flaws and stress corrosion. Flaws are unintentional imperfections formed during construction of the ring Examples of flaws include cracks, structural variations, pits, and other imperfections. Stress corrosion occurs when forces, pressures, stresses, and deleterious environments are imparted to the ring during its use. Examples of stress corrosion are staining, pitting, and cracking.

Retaining rings have traditionally been made as a single piece through seamless forging. This is done in order to provide the necessary combination of strength, toughness, homogeneity, and freedom from flaws required in the use and application of the retaining rings.

Retaining rings are usually assembled to a rotor with a shrink fit at one end of the ring. Additionally, an end plate is normally assembled to the other end of the retaining ring to provide access for balance weights and to stiffen the retaining ring in order to minimize non-cylindrical deformation from non-uniform winding loads. This end plate is also typically assembled to the retaining ring with a shrink fit.

The shrink fits at both ends of the retaining ring place the material at and near these shrink fits under maximum stresses when the rotor is at standstill or slow speed operation. Furthermore, even at synchronous speed, the overall maximum stresses do not dramatically change. As a result, stress corrosion can occur at any time.

Detection of flaws and stress corrosion in a retaining ring is extremely important because undetected defects may result in sudden failures causing extensive damage to the generator, the surrounding equipment, and personnel. One method for detecting flaws and stress corrosion in a retaining ring involves eddy current inspection of the inner surface of the ring.

Eddy current inspection is a non-destructive procedure used to detect flaws and stress corrosion in electrically conductive materials. This method involves placing an eddy current probe, comprising a coil, near the electrically conductive material. The coil sets up a magnetic field and induces eddy currents in the material. Defects in the material alter the eddy current flow and change the impedance of the coil. As a result, flaws and stress corrosion may be detected by moving the eddy current probe along the material and detecting changes of impedance of the coil.

Some previous scanning devices for eddy current inspection of retaining rings have not been automated. Because of the sensitivity of the probe and the lack of control in manipulation of the probe, these devices have suffered from probe lift off and probe wobble. As a result, these devices do not provide highly accurate detection of flaws and stress corrosion.

Other scanning devices have however been automated. One such device involves supporting an eddy current probe inside the ring for axial and rotational movement of the probe along the inner surface of the ring. This is accomplished by mounting two tripod shaped supports inside the ring. A drive rod is rotatably supported on the supports and an arm is fixed to the drive rod. A floor mounted drive assembly located away from the ring provides automated axial and rotational movement of the drive rod. Since the probe is mounted to the arm, it scans the inner surface for flaws and stress corrosion in a predetermined path between the support rods.

This prior art scanning device suffers from a number of limitations. First, since the supports are mounted inside the ring, the entire inner surface of the ring can not be inspected. Second, alignment of the drive rod along the axis of the ring is difficult to accomplish because horizontal adjustment of the tripod shaped supports necessarily affects vertical alignment, and visa versa. Furthermore, once the tripod shaped supports are aligned, alignment of the floor mounted drive assembly with the rotation axis of the supports is difficult to achieve and time consuming.

Thus, there is a need for a scanning device and method for automated eddy current inspection of retaining rings providing high reliability and the capability of time efficient inspection of the entire inner surface of the ring.

OBJECTS AND SUMMARY OF THE INVENTION

It is an object of the invention to provide quick and easy setup and alignment of a scanning device for automated inspection of retaining rings.

It is another object of the invention to provide an eddy current probe with rotational and axial motion for scanning the inner surface of a retaining ring.

It is a further object of the invention to provide the capability of scanning the entire inner surface of the retaining ring with an eddy current probe.

It is a further object of the invention to provide an apparatus which produces an optimal eddy current response.

It is still a further object of the invention to provide reliable control of an eddy current probe for minimizing probe lift off and wobble.

The foregoing and other objects of the invention are achieved by generally supporting an eddy current probe inside a retaining ring. The probe scans the entire inner surface of the ring while moving in an automated axial and rotational path within the ring.

More specifically, bracket mounting means are used to mount a pair of support brackets flush against the ends of the ring. A drive rod bearing is adjustably mounted to each support bracket by a bearing mount. A drive rod is journaled in the bearings and rotates inside the ring. The bracket mounting means are roughly adjust bearings so that the drive used to roughly aligned along the axis of the ring. The bearing mounts are used to precisely adjust the bearings. A scan arm is movably mounted to the drive rod so that the scan arm can move axially along the drive rod and rotate with the drive rod. An eddy current probe is attached to the end of the scan arm and scans the inner surface of the ring for flaws and stress corrosion while it is axially and rotationally moved within the cylindrical ring.

The foregoing and other objects of the invention will be more clearly understood from the following description taken in connection with the accompanying drawings.

DETAILED DESCRIPTION OF THE PREFERRED EMBODIMENT

Referring to the figures generally, an eddy current probe 11 is shown inspecting a ring 12 for flaws and stress corrosion. Probe 11 is supported inside ring 12 by a support structure mounted about the exterior of ring 12. The support structure enables probe 11 to scan along the inner surface 13 of ring 12 while moving in an automated axial and rotational path within ring 12.

Figure 1:
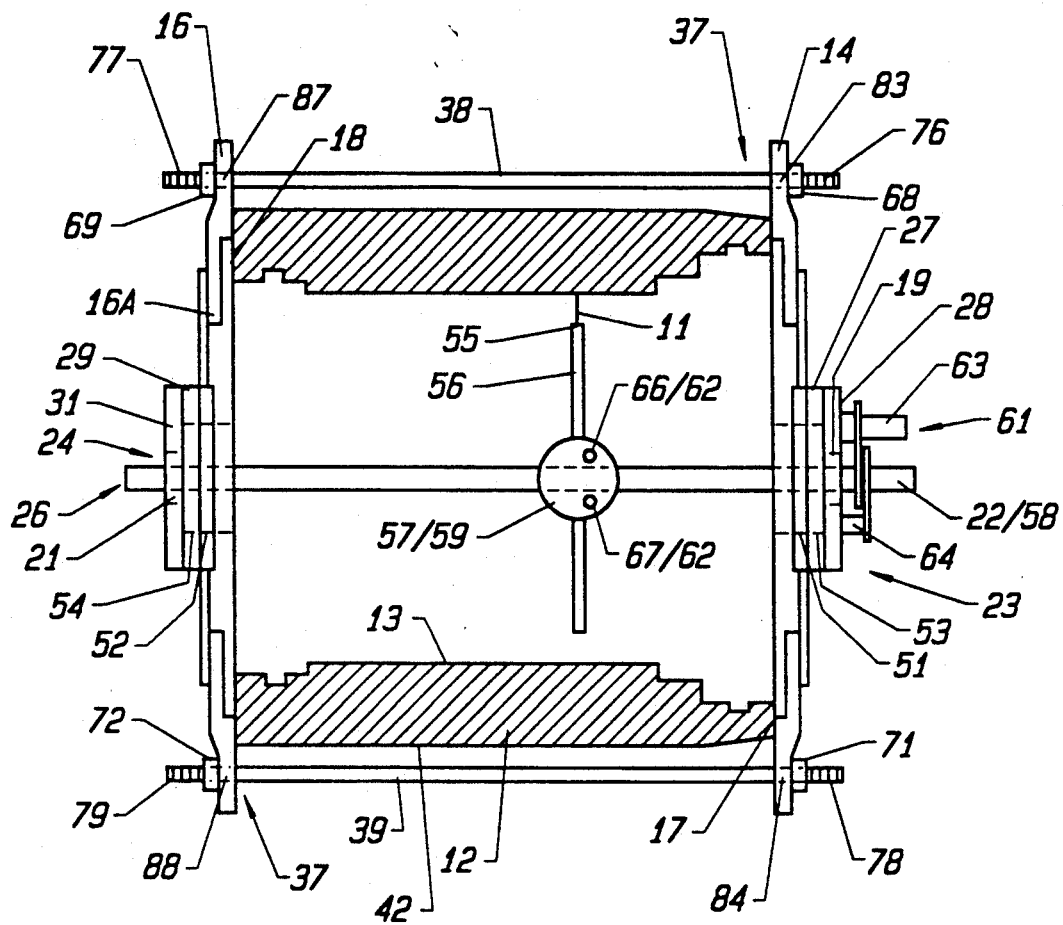
FIG. 1 is a cross sectional side view of the preferred embodiment of the invention.

As illustrated in FIG. 1, the support structure comprises spaced apart support brackets 14, 16. Bracket mounting means 37 is used for mounting bracket 14 flush against end 17 of ring 12 and for mounting bracket 16 flush against end 18 of ring 12. While the bracket mounts are flush against the ends of the ring, the plane of contact of bracket flanges 14A and 16A do not extend inward into the ring interior. Consequently, the brackets do not interfere with the eddy current probe 11 when the probe 11 is at either end of the ring. As a result, the entire inner surface 13 of ring 12 may be scanned.

The support structure also comprises drive rod bearings 19, 21, as shown in FIG. 1. Bearing 19 is adjustably mounted to support bracket 14 by bearing mount 23. Drive rod bearing 21 is adjustably mounted to support bracket 16 by bearing mount 24. A drive rod 22 is journaled in bearings 19 and 21 and rotates inside ring 12. Bearing mounts 23, 24 are used for precisely adjusting and centering bearings 19, 21 respectively so that rod 22 is aligned along axis 26 of ring 12. Bracket mounting means 37 is used for roughly adjusting and centering bearings 19, 21 respectively so that rod 22 is aligned along axis 26 of ring 12.

Figure 2:
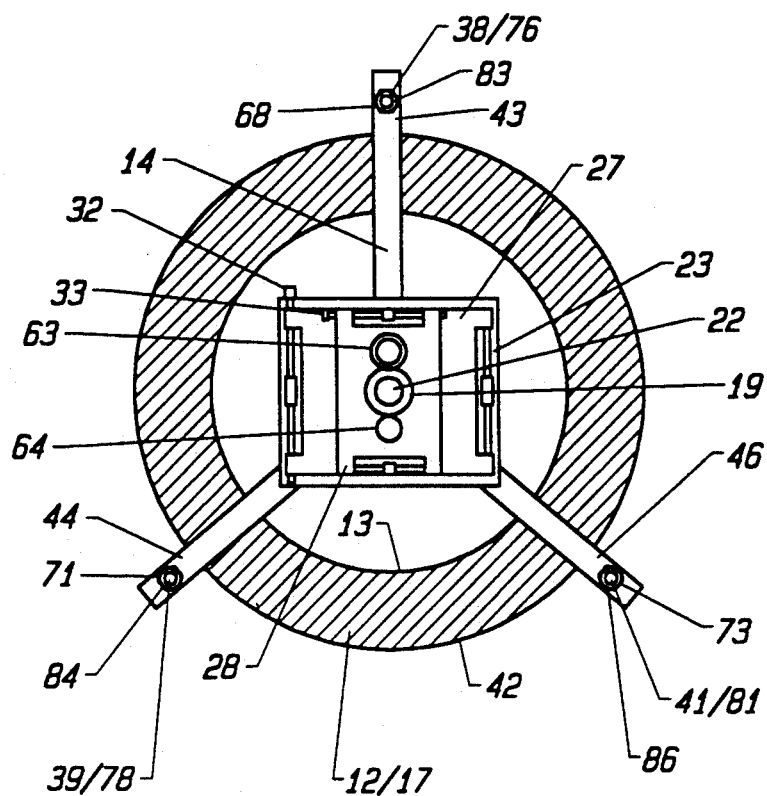
FIG. 2 is a front end view of the preferred embodiment of the invention.
Figure 3:
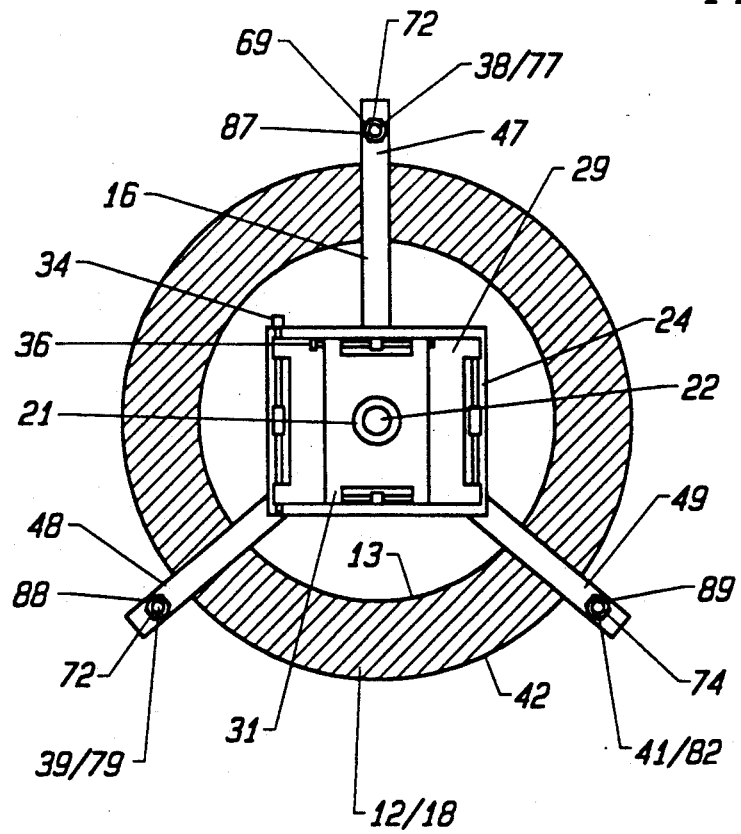
FIG. 3 is a back end view of the preferred embodiment of the invention.

In the preferred embodiment of the invention, bracket mounting means 37 comprises three connecting rods 38, 39, 41 and six nuts 68, 69, 71, 72, 73, 74, as illustrated in FIGS. 2 and 3. Connecting rods 38, 39, 41 are spaced apart around the outer surface 42 of ring 12. Bracket 14 has three spaced apart support arms 43, 44, 46 which extend out past the outer surface 42 of ring 12, as indicated in FIG. 2. Support arms 43, 44, 46 have holes 83, 84, 86 at their respective ends. And as shown in FIG. 3, bracket 16 has three support arms 47, 48, 49 which also extend out past the outer surface 42 of ring 12. Support arms 47, 48, 49 have holes 87, 88, 89 at their respective ends. Threaded ends 76, 77 of connecting rod 38 extend through holes 83, 87 respectively and are received by nuts 68, 69 respectively. Threaded ends 78, 79 of connecting rod 39 extend through holes 84, 88 respectively and are received by nuts 71, 72 respectively. Thread ends 81, 82 of connecting rod 41 extend through holes 86, 89 respectively and are received by nuts 73, 74 respectively. Connecting rods 38, 39, 41 are tensioned by turning nuts 68, 69, 71, 72, 73, 74 so that bracket 14 is forced against end 17 and bracket 16 is forced against end 18. Additionally, bearings 19, 21 adjusted and centered so that drive rod 22 is roughly aligned on the axis 26.

Support arms 43, 44, 46 on one end and 47, 48, 49 on the other end connect to bracket flanges, such as bracket flanges 16A and 14A shown in FIG. 1. The bracket flanges and support arms have holes which may be cooperatively aligned for fastening. To accommodate rings of different sizes, each of the support arms may be secured to a second extending arm piece (not shown) which provides additional arm length. Such a two piece arm allows for: (1) some adjustment to accommodate minor variations in ring size and (2) the use of different length arms to accommodate major differences in ring size.

Bracket mounting means 37 may also comprise a number of other alternatives. For example, rather than using three connecting rods, two, four, or more than four connecting rods may be employed. Furthermore, instead of using connecting rods, screw adjustments may be mounted about brackets 14, 16 so that the screws extend radially out over inner surface 13 or outer surface 42. In this case, support brackets 14, 16 are made large enough so as to extend out past outer surface 42. After brackets 14, 16 are placed against ends 17, 18 respectively, the screws are turned until they rest firmly against the surface over which they extend. Thus, support brackets 14, 16 are held firmly against ends 17, 18.

Also in the preferred embodiment, bearing mount 23 comprises adjustment plates 27, 28 and bearing mount 24 comprises adjustment plates 29, 31. FIGS. 1 and 2 show plate 27 slidably mounted to support bracket 14. Plate 28 is slidably mounted to plate 27 so that plates 27, 28 slide perpendicular to each other. Bearing 19 is mounted in plate 28. FIGS. 1 and 3 show plate 29 slidably mounted to bracket 16. Plate 31 is slidably mounted to plate 29 so that plates 29, 31 slide perpendicular to each other. Bearing 21 is mounted in plate 31. Brackets 14, 16 and plates 27, 29 have cut out portions 51, 52, 53, 54 respectively, as shown in FIG. 1. Drive rod 22 extends through cut out portions 51, 52, 53, 54 and bearings 19, 21. Plates 27, 28, 29, 31 all can be independently moved by turning screws 32, 33, 34, 36 respectively. As a result, bearings 19, 21 can be precisely adjusted and centered so that drive rod 22 is aligned on axis 26 of ring 12.

Bearing mounts 23, 24 may also comprise a two axis cross slide similar to that used to position parts in machining equipment.

As shown in FIG. 1, scan arm 56 is movably mounted to drive rod 22. Means 57 for movably mounting scan arm 56 to drive rod 22 allows scan arm 56 to be moved axially along drive rod 22 and rotate with drive rod 22.

Figure 4:
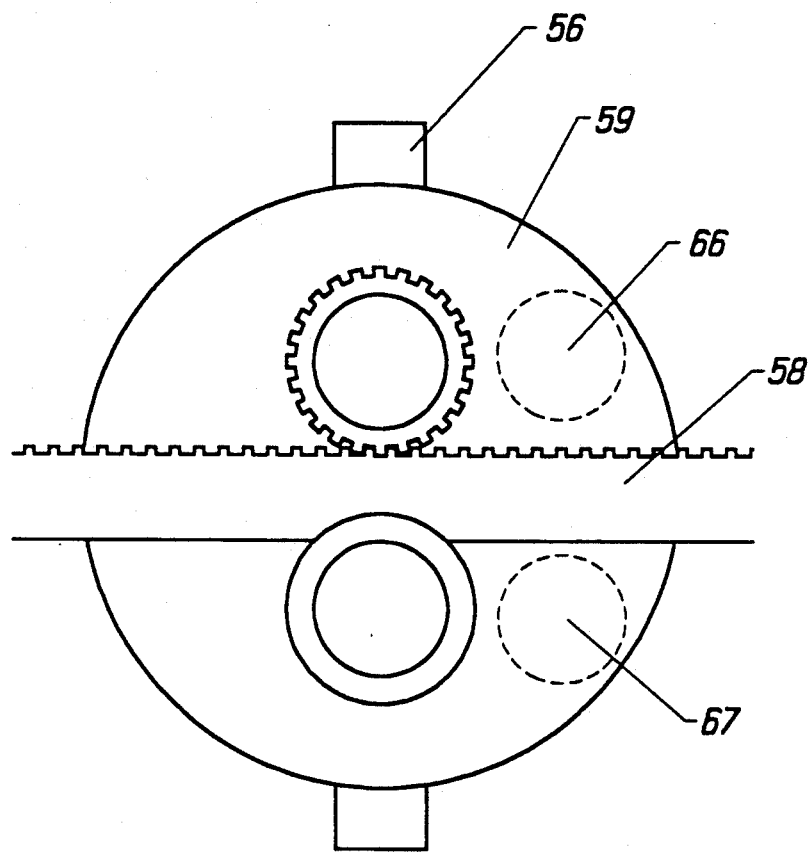
FIG. 4 is a cross sectional view of the point of attachment between the drive rod and the scan arm.

In the preferred embodiment, drive rod 22 includes a linear drive gear rack 58. Scan arm 56 comprises a linear gear drive bearing 59, as shown in FIG. 4, which is utilized to movably mount scan arm 56 to drive rod 22.

Drive rod 22 is rotated by drive means 61 and scan arm 56 is moved axially along drive rod 22 by drive means 62, as indicated in FIG. 1. As a result, rotation of drive rod 22 and axial movement of scan arm 56 is automated.

In the preferred embodiment of the invention, means 61 for rotating drive rod 22 comprises a rotary drive motor 63 and a rotary position encoder 64, as shown in FIGS. 1 and 2. Rotary drive motor 63 and rotary position encoder 64 are both mounted to either plate 28 or plate 31. Also, in the preferred embodiment, means 62 for moving scan arm 56 axially along drive rod 22 comprises an axial drive motor 66 and an axial position encoder 67, as shown in FIG. 4. Axial drive motor 66 and axial position encoder 67 are both mounted to linear gear drive bearing 59.

Eddy current probe 11 is attached to the end 55 of scan arm 56. Eddy current probe 11 scans inner surface 13 of ring 12 for flaws and stress corrosion while moving in an automated axial and rotational path inside ring 12. In the preferred embodiment, eddy current probe 11 scans in a raster type path.

As will be appreciated by one skilled in the art, the axial and rotational path followed by the eddy current probe 11 obtains an optimized eddy current response. Eddy current responses are strongest when the eddy current probe passes perpendicular to a flaw. That is, ideally, the eddy current probe is moved perpendicular to the length of a flaw. Since most corrosion cracks are aligned with the axis of the ring, it is advantageous to scan in a circumferential direction with an axial increment between scan passes. This is most readily accomplished, with minimum wear to scanning components and acceptable scan speed, when, as in the present invention, the scan is centrally driven with a rotary device as opposed to a prior art "crawler" scanner that is driven on the ring surface.

The foregoing descriptions of specific embodiments of the present invention have been presented for purposes of illustration and description. They are not intended to be exhaustive or to limit the invention to the precise forms disclosed. It is intended that the scope of the invention be defined by the claims appended hereto and their equivalents.

What is claimed is:

1. A scanning device for automated eddy current inspection of a retaining ring, comprising:
   a first end plate bracket;
   a second end plate bracket;
   means for clamping said first end plate bracket to the first end of said retaining ring;
   means for clamping said second end plate bracket to the second end of said retaining ring;
   a first drive rod mount coupled to said first end bracket;
   a second drive rod mount coupled to said second end bracket;
   a drive rod supported by said first drive rod mount and said second drive rod mount, said drive rod mount being supported coincident with the axis of said retaining ring;
   means for moving said drive rod;
   a scan arm supported on said drive rod, said scan arm extending radially from said drive rod;
   an eddy current probe positioned on the extending end of said scan arm; and
   means for moving said scan arm operating cooperatively with said means for moving said drive rod such that said eddy current probe moves along the interior surface of said retaining ring.

2. The apparatus of claim 1 wherein said means for moving said drive rod includes a rotary drive motor and a rotary position encoder.

3. The apparatus of claim 1 wherein said means for moving said scan arm includes an axial drive motor and an axial position encoder.

4. The apparatus of claim 1 wherein said first drive rod mount is adjustable to accommodate different sizes of said retaining ring.

5. The apparatus of claim 1 wherein said second drive rod mount is adjustable to accommodate different sizes of said retaining ring.

6. A scanning device for automated eddy current inspection of retaining rings having an axis, a first and a second end, and an inner and an outer surface, comprising:
   a drive rod;
   means for automatedly rotating said drive rod;
   a first and a second support bracket;
   a first and a second drive rod bearing, said drive rod being journaled in said bearings;
   a first bearing mount for adjustably mounting said first bearing to said first bracket and a second bearing mount for adjustably mounting said second bearing to said second bracket, said first and second bearing mounts being used to precisely adjust and center said bearings so that said drive rod is aligned on said axis of said ring;
   bracket mounting means for mounting said first bracket flush against said first end of said ring and for mounting said second bracket flush against said second end of said ring, whereby all of said inner surface of said ring may be scanned, said bracket mounting means also being used to roughly adjust and center said bearings so that said drive rod is aligned on said axis of said ring;
   a scan arm having an end;
   means for movably mounting said scan arm to said drive rod so that said scan arm moves axially along said drive rod and rotates with said drive rod;
   means for automatedly moving said scan arm axially along said drive rod; and
   an eddy current probe mounted to said end of said scan arm, said probe scanning said inner surface of said ring for flaws and stress corrosion while moving axially and rotationally inside said ring.

7. A scanning device as in claim 6 wherein said means for rotating said drive rod includes a rotary drive motor and a rotary position encoder.

8. A scanning device as in claim 6 wherein said means for moving said scan arm axially along said drive rod includes an axial drive motor and an axial position encoder.

9. A scanning device as in claim 6 wherein said first bracket comprises three support arms and said second bracket comprises three support arms.

10. A scanning device as in claim 6 wherein said first bearing mount comprises a first and a second adjustment plate and said second bearing mount comprises a third and a fourth adjustment plate, said first plate being slidably mounted to said first bracket, said second plate being slidably mounted to said first plate so that said first and second plates slide perpendicular to each other, said first bearing being mounted in said second plate, said third plate being slidably mounted to said second bracket, said fourth plate being slidably mounted to said third plate so that said third and fourth plates slide perpendicular to each other, said second bearing being mounted in said fourth plate, said first, second, third, and fourth plates being slidably shifted to precisely adjust and center said bearings so that said rod is aligned on said axis of said ring.

11. A scanning device as in claim 10 wherein said first and third plates and said first and second brackets all have cut out portions, said drive rod extending through said cut out portions and said bearings.

12. A scanning device as in claim 6 wherein said drive rod comprises a linear drive gear rack and said means for movably mounting said scan arm to said drive rod comprises a linear gear drive bearing.

13. A method for automated eddy current inspection of a retaining ring having an axis, a first and a second end, and an inner and an outer surface, comprising the steps of:

mounting a first support bracket flush against said first end of said ring and mounting a second support bracket flush against said second end of said ring, whereby all of said inner surface of said ring may be scanned;

adjustably mounting a first drive rod bearing to said first bracket and adjustably mounting a second drive rod bearing to said second bracket;

journaling a drive rod in said first and second drive rod bearings;

adjusting said bearings so that said drive rod is aligned on said axis of said ring;

movably mounting a scan arm to said drive rod so that said scan arm can move axially along said drive rod and rotate with said drive rod, said scan arm having an end;

mounting an eddy current probe to said end of said scan arm;

automatedly rotating said drive rod;

automatedly moving said scan arm axially along said drive;

scanning said inner surface of said ring for flaws and stress corrosion with said eddy current probe, said eddy current probe moving in an automated axial and rotational path within said cylindrical ring during said step of scanning.

14. A method as in claim 13 wherein said step of rotating said drive rod is made with a rotary drive motor and a rotary position encoder.

15. A method as in claim 13 wherein said step of moving said scan arm axially along said drive rod is made with an axial drive motor and an axial position encoder.

* * * * *